US00PP23208P3

(12) United States Plant Patent
van Dijk

(10) Patent No.: US PP23,208 P3
(45) Date of Patent: Nov. 20, 2012

(54) *ANTHURIUM* PLANT NAMED 'ANTHULYHA'

(50) Latin Name: *Anthurium andreanum L.*
Varietal Denomination: Anthulyha

(75) Inventor: Jan van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 13/066,334

(22) Filed: Apr. 11, 2011

(65) Prior Publication Data

US 2012/0260378 P1 Oct. 11, 2012

(51) Int. Cl.
*A01H 5/00* (2006.01)

(52) U.S. Cl. ..... Plt./365

(58) Field of Classification Search ..... Plt./365
See application file for complete search history.

*Primary Examiner* — Kent L Bell

(74) *Attorney, Agent, or Firm* — Jondle & Associates, P.C.

(57) ABSTRACT

A new *Anthurium* plant particularly distinguished by having pale-pink colored spathes with pink-red towards the tip and edge of the spathes, spathes that slowly turn green with age, a compact and full plant habit, rich shoot formation, and a plant height of about 40.0 cm to 50.0 cm, is disclosed.

3 Drawing Sheets

Genus and species: *Anthurium andreanum* L.
Variety denomination: 'Anthulyha'.

BACKGROUND OF THE NEW PLANT

The present invention comprises a new and distinct variety of *Anthurium*, botanically known as *Anthurium andreanum* L., and hereinafter referred to by the variety name 'Anthulyha'. The new variety originated from a hybridization made in September 2000 in Bleiswijk, The Netherlands. The female parent was an *Anthurium* plant '95-634-01' (unpatented), while the male parent was a purple *Anthurium* plant '97-1173-03' (unpatented).

A single plant was selected in July 2002 and has been asexually reproduced repeatedly by tissue culture in Bleiswijk, The Netherlands over a five-year period. The present invention has been found to retain its distinctive characteristics through successive asexual propagations.

Plant Breeder's Rights for this variety were applied for in the European Union on Nov. 30, 2007, in Japan on Mar. 9, 2010, and in China on Mar. 22, 2010. 'Anthulya' has not been made publicly available more than one year prior to the filing of this application.

SUMMARY OF THE INVENTION

The following are the most outstanding and distinguishing characteristics of this new variety when grown under normal horticultural practices in Bleiswijk, The Netherlands.

1) Pale-pink colored medium sized spathes with a pink-red edge;
2) Purple spadix;
3) Rich shoot formation; and
4) Compact plant habit.

DESCRIPTION OF THE PHOTOGRAPHS

This new *Anthurium* plant is illustrated by the accompanying photographs; the colors shown are as true as can be reasonably obtained by conventional photographic procedures. The photographs are of a 48-week old plant grown in a greenhouse in Bleiswijk, The Netherlands in 2009.

DESCRIPTION OF THE NEW VARIETY

Figure 1:
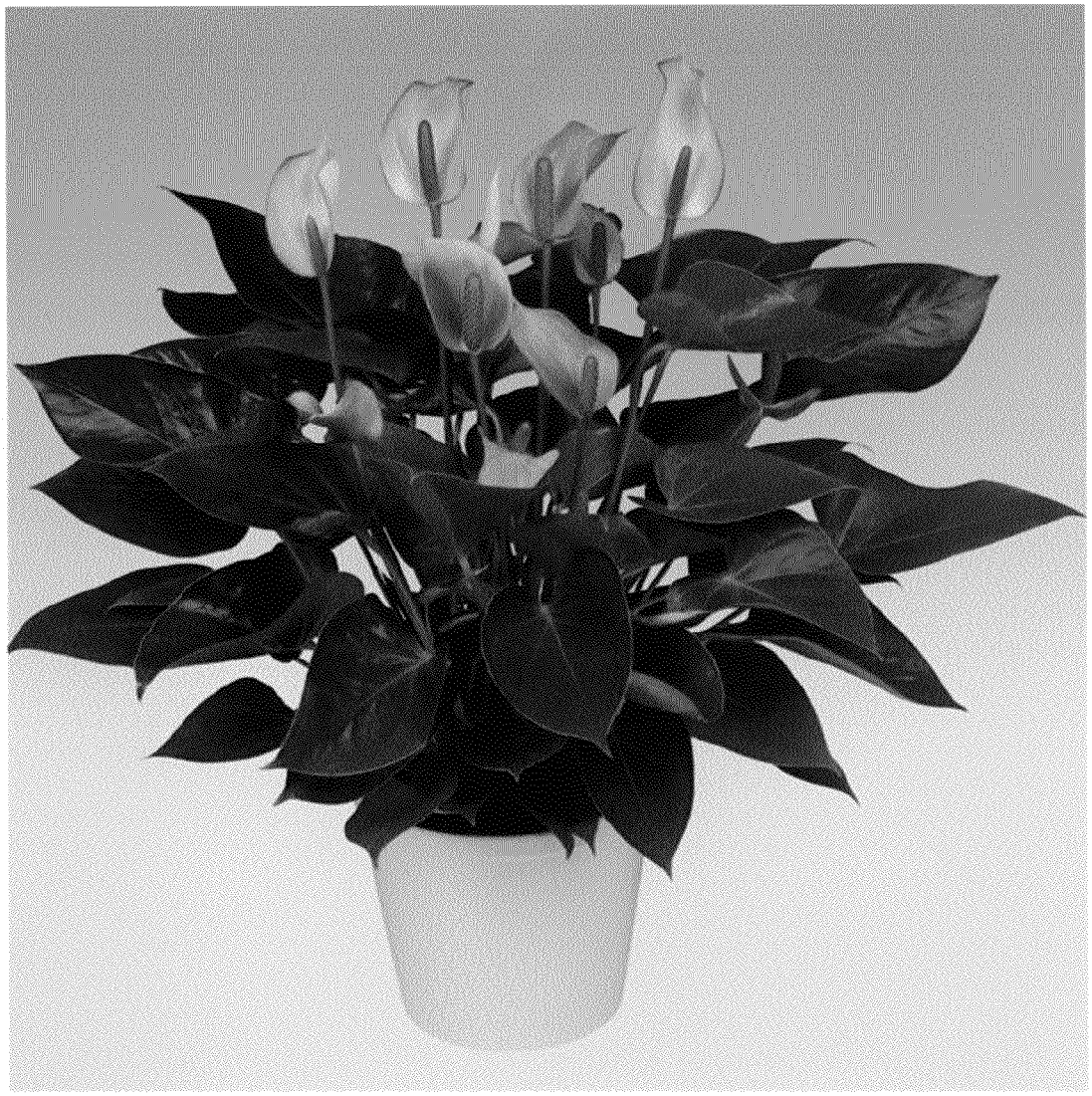
FIG. 1 shows the overall plant habit, including blooms, buds and foliage.
Figure 2:
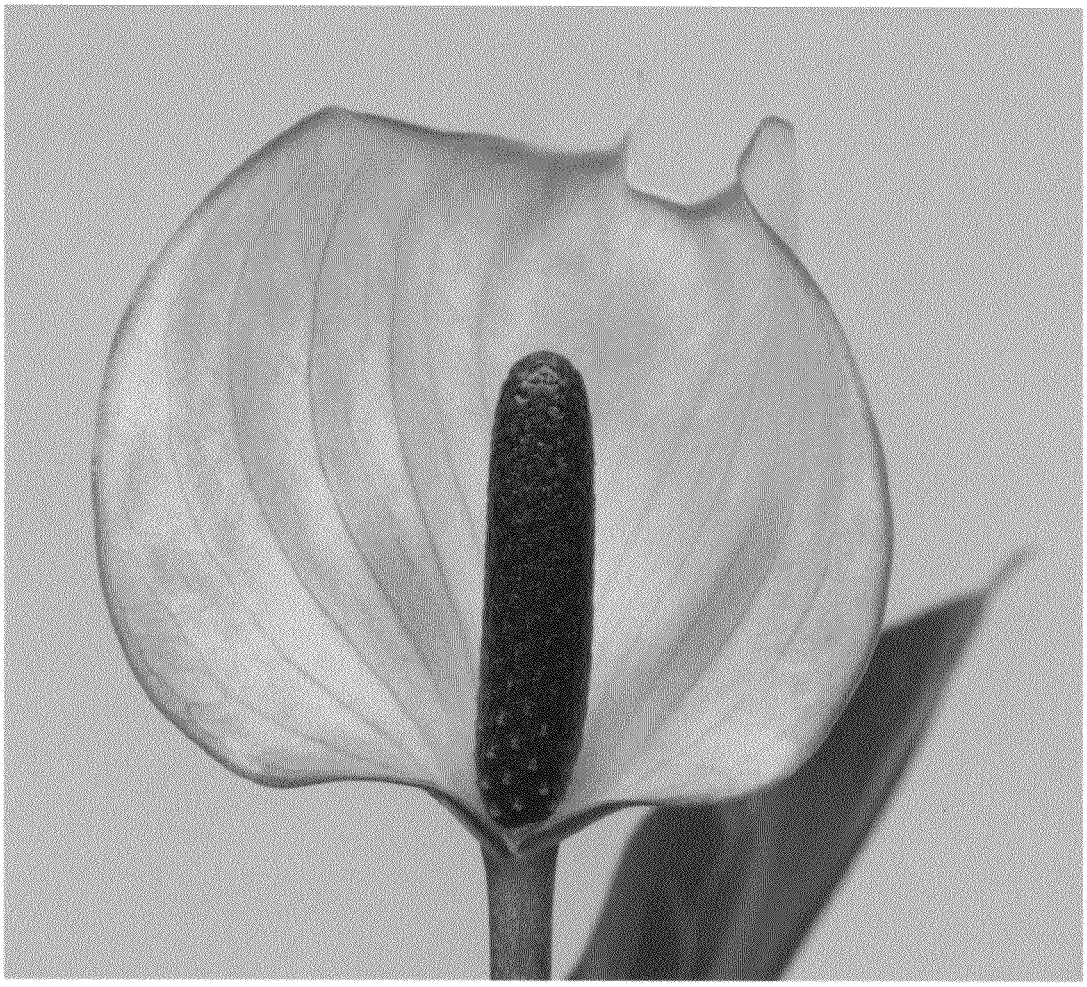
FIG. 2 is a close-up of the mature spathe.
Figure 3:
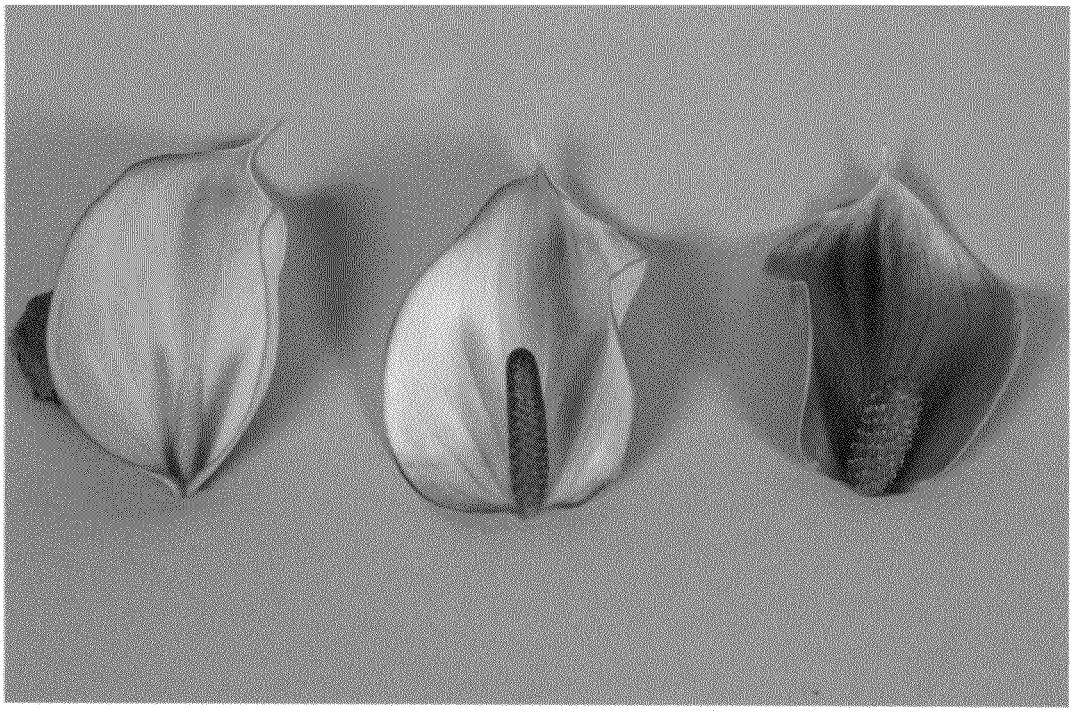
FIG. 3 shows three spathes at different stages of development.
Figure 4:
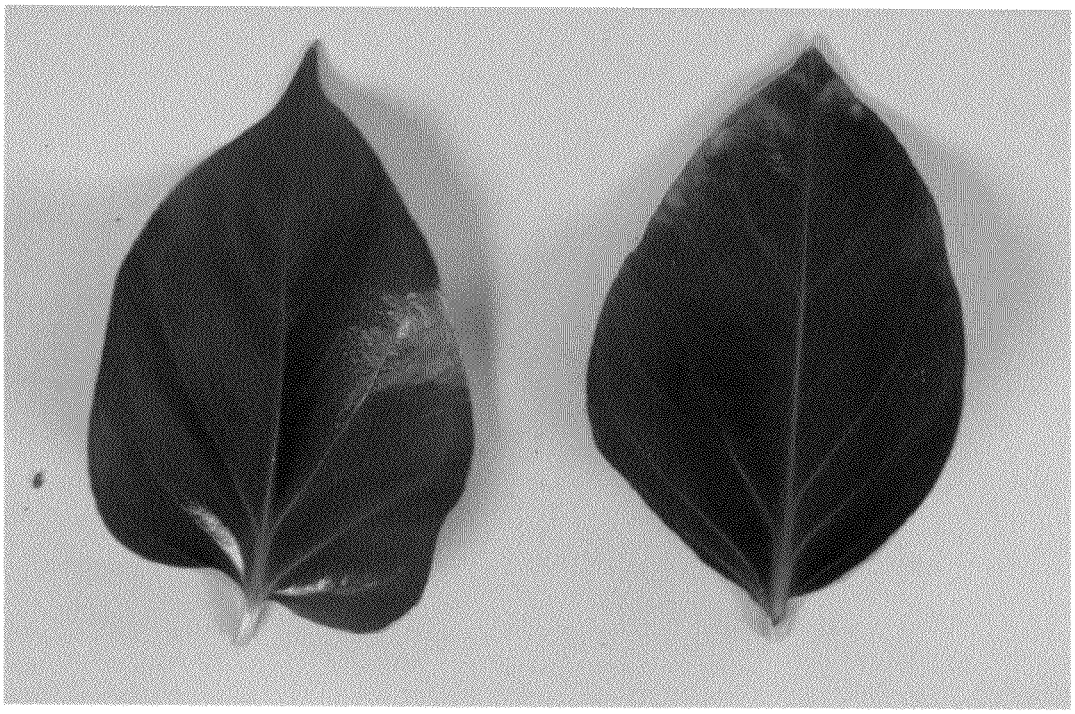
FIG. 4 shows the upper and lower leaf surfaces.

The following detailed description sets forth the distinctive characteristics of 'Anthulyha'. The data which define these characteristics were collected from asexual reproductions carried out in Bleiswijk, The Netherlands. The plant history was taken on 48-week old plants which were planted from tissue culture in 17 centimeter pots and grown in a glass greenhouse between 19° C. and 24° C. Observations were made in November of 2009. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family*.—Araceae.
- *Botanical*.—*Anthurium andreanum* L.
- *Common name*.—*Anthurium*.

Parentage:
- *Female parent*.—*Anthurium* plant '95-634-01' (unpatented).
- *Male parent*.—*Anthurium* plant '97-1173-03' (unpatented).

Plant:
- *Propagation*.—Tissue culture.
- *Root description*.—Fleshy cream-colored roots with smaller hairy lateral roots that are yellow-tipped.
- *Time to produce a finished flowering plant*.—45 to 50 weeks for a 17.0 cm pot.
- *Growth habit*.—Herbaceous perennial.

*Height* (*measured from soil, including inflorescence*).—40.0 cm to 50.0 cm.

*Width* (*measured from leaf tips*).—40.0 cm to 45.0 cm.

Leaves:

*Immature leaves*.—Length: 7.0 cm to 12.0 cm. Width: 4.0 cm to 8.0 cm. Color: Upper surface: RHS 137A. Lower surface: RHS 137B. Texture (both upper and lower surfaces): Shiny.

*Mature leaves*.—Length (fully expanded): 15.0 cm to 18.0 cm. Width: 10.0 cm to 12.0 cm. Shape: Elliptical-cordate, weakly cupped. Apex: Acuminate. Base: Cordate. Leaf blade angle with the petiole: Between 130 degrees and 160 degrees. Leaf margin: Entire. Color: Upper surface: RHS 139A. Lower surface: RHS 137B. Texture (both upper and lower surfaces): Shiny, leathery and thick; very weakly blistered to not blistered. Venation: Pinnate with protruding primary and mid-veins at the underside of the leaf blade. Venation color: Upper surface: RHS 137C. Lower surface: RHS 145A.

*Lobes*.—Arrangement: Leaf blade has two large lobes extending past the petiole. Length of lobes of mature leaf blades: 1.0 cm to 2.0 cm. Width of lobes of mature leaf blades: 4.5 cm to 5.5 cm. Distance from petiole/leaf junction to highest point on lobes of mature leaf blades: 3.5 cm to 4.5 cm.

*Petiole*.—Cross-section: Round. Diameter: 0.3 cm to 0.4 cm. Length: 17.0 cm to 22.0 cm for a mature leaf size. Color: Mature leaf: RHS 146B. Immature leaf: RHS 146B. Cataphyl color surrounding the petiole: Outside: RHS 184A. Inside: RHS 184C.

*Geniculum*.—Length: 1.0 to 2.0 cm. Width: 0.4 cm to 0.5 cm. Color: 146C to RHS 186A.

Inflorescence:

*Arrangement*.—Single.

*Flowering habit* (*length of flowering season*).—Continuous.

*Number of inflorescences per plant*.—10 to 14.

*Fragrance*.—Absent.

*Longevity of inflorescence on plant*.—Greater than one year.

*Longevity of the flower as a cut flower*.—Not observed.

Spathe:

*Buds*.—The spathe is tightly rolled around the spadix and extrudes from the peduncle sheath. After the spathe is fully opened the peduncle elongates by several centimeters.

*Arrangement*.—The spathe angle with the peduncle is between 120 degrees and 140 degrees; the spathe stands on a slightly curved wiry peduncle about 5.0 cm to 9.0 cm above the foliage.

*Shape*.—Oblong-cordate with a flat (not blistered) surface.

*Apex*.—Cuspidate tip.

*Base*.—Sub-cordate.

*Texture* (*both surfaces*).—Unblistered.

*Glossiness*.—Very weak to weak.

*Margin*.—Entire.

*Size*.—Height (peduncle length at maturity): 25.0 cm to 30.0 cm. Length: 8.0 cm to 10.0 cm. Width: 5.0 cm to 7.0 cm.

*Color*.—Upper surface: Main color pale-pink, RHS 54D. Veins have a more intense color. Color becomes RHS 54C towards the margin. The margin itself is dark pink red (RHS 51A). Older spathes become darker green (RHS 144A). Lower surface: RHS 156C (white) to RHS 63A (red) at the rim.

Peduncle:

*Shape*.—Erect.

*Cross-section*.—Round.

*Length*.—25.0 cm to 30.0 cm.

*Diameter*.—0.3 cm to 0.5 cm.

*Color*.—RHS 146B at unrolling of spathe, slowly turning RHS 138A when the spathe matures.

Flowering time:

*General*.—A small rooted untreated tissue culture plant of 2.0 cm tall will flower after 6 to 8 months and 2 to 3 blossoms appear (depending on the season). More blossoms appear after additional weeks. A full flowering commercial plant has 10 to 14 pale-pink to green spathes. Smaller blossoms may occur on less mature plants.

Spadix:

*Size*.—Length: 2.5 cm to 4.5 cm. Width (at apex): 0.5 cm to 0.8 cm. Width (at base): 0.7 cm to 0.9 cm.

*Shape*.—Columnar.

*Angle of spadix tip with peduncle*.—180 degrees (spadix is in one line with peduncle).

*Texture*.—When the spathe is unfurling: Smooth. When the spadix matures: Very small stigmata protrude.

*Distribution of stigmata*.—Evenly distributed around the spadix.

*Spadix maturity*.—Matures from base to top, slowly giving the spadix a somewhat rough appearance.

*Color*.—Immature: RHS 71B. Mature: RHS 71A. Ages to: RHS 157A.

Flowers:

*Quantity per spadix*.—200 to 250.

*Spadix flower arrangement*.—Bisexual, rounded in cross-section.

*Shape*.—Rounded.

*Size*.—Length: 0.1 cm to 0.2 cm. Diameter (maximum): 0.2 cm. Color: RHS 71A.

Reproductive organs:

*Stamens*.—None visible.

*Pollen*.—Sparse.

*Pollen color*.—RHS 156D.

*Pistil*.—Quantity: Many. Length: Less than 0.01 cm. Color: RHS 71A.

*Style*.—None observed.

*Stigma*.—Shape: Ovoid. Diameter: Less than 0.01 cm. Color: RHS 155D.

*Ovary*.—Rarely visible.

*Ovary color*.—RHS 155A.

Fruit and Seed Set: None observed.

COMPARISON WITH PARENTAL AND COMMERCIAL VARIETIES

'Anthulyha' differs from the female parent, '95-634-01', in that its spathe has pale-pink color (RHS 54D), with a pink-red colored rim, while the spathe of '95-634-01' is pinkish red (RHS 52B). Further, the spathe of 'Anthulyha' has a very weak to weak glossiness, while the spathe of '95-634-01' has medium glossiness.

'Anthulyha' differs from the male parent '97-1173-03' (unpatented) in that 'Anthulyha' has a much smaller plant habit, smaller spathes, and smaller leaves than '97-1173-03'. Additionally, 'Anthulyha' has a main spathe color of RHS 54D, while the spathe color of '97-1173-03' is RHS 52B.

The new variety 'Anthulyha' can be compared to the commercial variety 'Pink Champion' (U.S. Plant Pat. No.

12,115). 'Anthulyha' differs from 'Pink Champion' in that 'Anthulyha' has a spathe color of RHS 54D, which becomes RHS 51A at the spathe margin, while the spathe color of 'Pink Champion' is RHS 52B. Additionally, the spadix color of 'Anthulyha' is RHS 71A, while the spadix color of 'Pink Champion' is RHS 48B.

TABLE 1

Comparison of characteristics between 'Anthulyha' and 'Pink Champion'

| Characteristic | 'Anthulyha' | 'Pink Champion' |
|---|---|---|
| Spathe color | RHS 54D to RHS 51A (at margin) | RHS 52B |
| Spadix color | RHS 71A | RHS 48B |

TABLE 1-continued

Comparison of characteristics between 'Anthulyha' and 'Pink Champion'

| Characteristic | 'Anthulyha' | 'Pink Champion' |
|---|---|---|
| Leaf length | 15.0-18.0 cm | 17.0-21.0 cm |
| Shoot formation | Medium | Strong |

I claim:

1. A new and distinct variety of *Anthurium* plant named 'Anthulyha' as shown and described herein.

* * * * *